US012780763B2

(12) United States Patent
Zellhuber et al.

(10) Patent No.: US 12,780,763 B2
(45) Date of Patent: Nov. 3, 2026

(54) METHOD AND PLANT FOR PRODUCING A TARGET COMPOUND

(71) Applicants: LINDE GMBH, Pullach (DE); Clariant International Ltd., Muttenz (CH)

(72) Inventors: Mathieu Zellhuber, Martinsried (DE); Martin Schubert, Munich (DE); Andreas Meiswinkel, Rimsting (DE); Wolfgang Muller, Munich (DE); Ernst Haidegger, Riemerling (DE); Gerhard Mestl, Bruckmühl (DE); Klaus Wanninger, Bruckmühl (DE); Peter Scheck, Munich (DE)

(73) Assignees: Linde GmbH, Pullach (DE); Clariant International Ltd., Muttenz (CH)

( * ) Notice: Subject to any disclaimer, the term of this patent is extended or adjusted under 35 U.S.C. 154(b) by 388 days.

(21) Appl. No.: 18/549,583

(22) PCT Filed: Mar. 14, 2022

(86) PCT No.: PCT/EP2022/056572
§ 371 (c)(1),
(2) Date: Sep. 7, 2023

(87) PCT Pub. No.: WO2022/194794
PCT Pub. Date: Sep. 22, 2022

(65) Prior Publication Data

US 2024/0150261 A1 May 9, 2024

(30) Foreign Application Priority Data

Mar. 15, 2021 (DE) ......................... 102021202505.6

(51) Int. Cl.
*C07C 5/48* (2006.01)
*B01J 19/00* (2006.01)
*C07C 5/32* (2006.01)

(52) U.S. Cl.
CPC ........... *C07C 5/324* (2013.01); *B01J 19/0013* (2013.01); *C07C 2523/22* (2013.01); *C07C 2523/28* (2013.01); *C07C 2527/057* (2013.01)

(58) Field of Classification Search
CPC ........... C07C 5/333; C07C 5/48; C07C 5/324; C07C 2523/20; C07C 2523/22;
(Continued)

(56) References Cited

U.S. PATENT DOCUMENTS 8,519,210 B2 8/2013 Arnold et al.
10,836,689 B2 * 11/2020 Cizeron ..................... B01J 8/06
(Continued)

FOREIGN PATENT DOCUMENTS

CA 3100928 A1 * 12/2019 ............ B01J 8/0496
DE 19837519 A1 2/2000
(Continued)

OTHER PUBLICATIONS

International Search Report and Written Opinion issued in related App. No. PCT/EP2022/056572, mailed Jul. 7, 2022.
(Continued)

*Primary Examiner* — In Suk C Bullock
*Assistant Examiner* — Jason Y Chong
(74) *Attorney, Agent, or Firm* — Avek IP, LLC

(57) ABSTRACT

A method for producing a target compound, includes distributing feed mixture at a temperature in a first temperature range to a plurality of parallel reaction tubes of a shell-and-tube reactor. The method further includes subjecting the feed mixture in first tube sections of the reaction tubes to heating to a temperature in a second temperature range, and in
(Continued)

second tube sections of the reaction tubes arranged downstream of the first tube sections to oxidative catalytic conversion using one or more catalysts arranged in the second tube sections. The heating is performed, at least in part, using a catalyst arranged in the first tube sections and having a light-off temperature in the first temperature range.

19 Claims, 4 Drawing Sheets

(58) Field of Classification Search

CPC .................... C07C 2523/28; C07C 2527/057; B01J 8/06; B01J 2208/00017; B01J 2208/00212; B01J 2208/0053; B01J 2208/00548; B01J 2208/021; B01J 2208/025; B01J 2219/00033; B01J 19/30; B01J 19/0013; B01J 27/0576; B01J 35/612; B01J 35/613; B01J 35/633; B01J 37/0036; B01J 37/009; B01J 37/031; B01J 37/033; B01J 37/088; B01J 23/28; Y02P 20/52

See application file for complete search history.

(56) References Cited

U.S. PATENT DOCUMENTS

| | | | |
|---|---|---|---|
| 11,014,075 | B2 | 5/2021 | Mestl et al. |
| 11,401,220 | B2 | 8/2022 | Bos et al. |
| 12,012,377 | B2 | 6/2024 | Zellhuber et al. |
| 2010/0256432 | A1 | 10/2010 | Arnold et al. |
| 2015/0321974 | A1 | 11/2015 | Schammel et al. |
| 2017/0233313 | A1 | 8/2017 | Grüne et al. |
| 2018/0170838 | A1 | 6/2018 | Cao et al. |
| 2019/0055177 | A1 | 2/2019 | Bos et al. |
| 2024/0150261 | A1 | 5/2024 | Zellhuber et al. |
| 2024/0150263 | A1 | 5/2024 | Zellhuber et al. |
| 2024/0158322 | A1 | 5/2024 | Zellhuber et al. |
| 2024/0294447 | A1 | 9/2024 | Zellhuber et al. |

FOREIGN PATENT DOCUMENTS

| | | | |
|---|---|---|---|
| DE | 102017000848 | A1 | 8/2018 |
| DE | 102017000861 | A1 | 8/2018 |
| EP | 1164120 | A2 | 12/2001 |
| EP | 2716621 | A1 | 4/2014 |
| EP | 2716622 | A1 | 4/2014 |
| EP | 3339277 | A1 | 6/2018 |
| EP | 3476471 | A1 | 5/2019 |
| EP | 3558910 | A1 | 10/2019 |
| EP | 3558910 | B1 | 10/2019 |
| RU | 2214383 | C1 | 10/2003 |
| RU | 2335485 | C2 | 10/2008 |
| RU | 2730518 | C2 | 8/2020 |
| WO | 2010115099 | A1 | 10/2010 |
| WO | 2013021034 | A1 | 2/2013 |
| WO | 2013164418 | A1 | 11/2013 |
| WO | 2017144584 | A1 | 8/2017 |
| WO | 2018082945 | A1 | 5/2018 |
| WO | 2018115416 | A1 | 6/2018 |
| WO | 2018115418 | A1 | 6/2018 |
| WO | 2018141652 | A1 | 8/2018 |
| WO | 2018141653 | A1 | 8/2018 |
| WO | 2019243480 | A1 | 12/2019 |
| WO | 2020072163 | A1 | 4/2020 |
| WO | 2020074750 | A1 | 4/2020 |

OTHER PUBLICATIONS

Substantive examination report with English description issued Oct. 20, 2025 in Saudi Arabia Application No. 523450721, 10 pages.

Sanfiz et al., Preparation of Phase-Pure M1 MoVTeNb Oxide Catalysts by Hydrothermal Synthesis-Influence of Reaction Parameters on Structure and Morphology. Top Catal (2008) 50:19-32 (Year: 2008), 14 pages.

Yingzhen, Zhang, Study on Selective Oxidation of Propane by Composite Metal Oxides, China Master's Theses Full-text Database (Engineering & Technology I), Feb. 15, 2006, B016-5, 6 pages.

* cited by examiner

METHOD AND PLANT FOR PRODUCING A TARGET COMPOUND

CROSS-REFERENCE TO RELATED APPLICATIONS

This application is the national phase of, and claims priority to, International Application No. PCT/EP2022/056572, filed Mar. 14, 2022, which claims priority to German Application No. DE102021202505.6, filed Mar. 15, 2021.

FIELD OF THE INVENTION

The invention relates to a method and a plant for producing a target compound.

BACKGROUND

Oxidative dehydrogenation (ODH) of alkanes having two to four carbon atoms is generally known. During the ODH, said alkanes are converted with oxygen, inter alia, to give the respective olefins and water. The invention relates in particular to the oxidative dehydrogenation of ethane to ethylene, hereinafter also referred to as ODHE. However, the invention is in principle not limited to the oxidative dehydrogenation of ethane, but may also extend to the oxidative dehydrogenation (ODH) of other alkanes such as propane or butane. The following explanations apply accordingly in this case.

ODH(E) may be advantageous over more established methods for producing olefins, such as steam cracking or catalytic dehydrogenation. For instance, due to the exothermic nature of the reactions involved and the practically irreversible formation of water, there is no thermodynamic equilibrium limitation. The ODH(E) can be carried out at comparatively low reaction temperatures. In principle, no regeneration of the catalysts used is required, since the presence of oxygen enables or causes regeneration in situ. Finally, in contrast to steam cracking, lower amounts of valueless by-products, such as coke, are formed.

For further details regarding ODH(E), reference may be made to relevant literature, for example Ivars, F. and López Nieto, J. M., Light Alkanes Oxidation: Targets Reached and Current Challenges, in Duprez, D. and Cavani, F. (eds.), Handbook of Advanced Methods and Processes in Oxidation Catalysis: From Laboratory to Industry, London 2014: Imperial College Press, pages 767-834, or Gärtner, C. A. et al, Oxidative Dehydrogenation of Ethane: Common Principles and Mechanistic Aspects, ChemCatChem, vol. 5, no. 11, 2013, pages 3196 to 3217, and X. Li, E. Iglesia, Kinetics and Mechanism of Ethane Oxidation to Acetic Acid on Catalysts Based on Mo—V-Nb Oxides, J. Phys. Chem. C, 2008, 112, 15001-15008.

In particular, MoVNb-based catalyst systems have shown promise for ODH(E), as mentioned, for example, in F. Cavani et al, "Oxidative dehydrogenation of ethane and propane: How far from commercial implementation?", Catal. Today, 2007, 127, 113-131. Catalyst systems additionally containing Te can also be used. Where reference is made herein to a "MoVNb-based catalyst system" or a "MoVTeNb-based catalyst system", this shall be understood to mean a catalyst system which has the elements mentioned as a mixed oxide, also expressed as $MoVNbO_x$ or $MoVTeNbO_x$, respectively. Where Te is given in brackets, this indicates its optional presence. The invention is used in particular with such catalyst systems.

During the ODH, particularly when $MoVNb(Te)O_x$-based catalysts are used under industrially relevant reaction conditions, significant amounts of the respective carboxylic acids of the alkanes used, in particular acetic acid in the case of ODHE, are formed as by-products. For the economical operation of the plant, co-production of olefins and the carboxylic acids is therefore generally unavoidable when using the catalyst type described.

The required use of oxygen as oxidant in ODH(E), in particular in low dilution conditions, can in principle lead to explosive mixtures within the plant. Mixing concepts that can be used here to avoid explosive mixtures in certain plant parts or reactor regions are known and are described, for example, in EP 3 476 471 A1 for a commercial shell-and-tube reactor; however, in addition to structural measures (e.g., the plant of flame or detonation barriers, the minimization of free volumes, pressure-resistant design), these or other approaches require in particular that the corresponding ignition temperature is far from being reached before the actual reactor.

According to the prior art, the ODH(E) is preferably carried out in fixed-bed reactors, in particular in cooled shell-and-tube reactors, e.g., with molten salt cooling. For highly exothermic reaction, i.e., in particular oxidative reactions, which also includes ODH(E), the use of a reactor bed with several zones is generally known. Basic principles are described, for example, in WO 2019/243480 A1 by the applicant. This document discloses the principle that different catalyst beds or corresponding reaction zones, which have different catalyst loadings and/or catalyst activities per spatial unit, are used.

According to the prior art, further heating takes place only in the reactor, and more precisely only in the respective reaction tubes themselves, in order to reach the inlet temperature into the active (single- or multi-layer) catalyst bed (e.g., according to the already cited WO 2019/243480 A1). For this purpose, an inert bed is introduced in the inlet zone which is sufficiently long to ensure effective heating of the gas flow. Details in this regard are explained below Furthermore, however, particularly effects of trace components which may be contained in the reaction feed must also be taken into account in the design of a corresponding method. As is true for all heterogeneously catalyzed processes, it is also true for oxidative methods and in particular for ODH(E) and the catalysts used here that certain components act as so-called catalyst poisons and lead to a gradual reduction in the activity and/or selectivity of the catalyst ("catalyst poisoning") up to and including complete deactivation.

These effects occur initially and in particular at the beginning of the active catalyst filling. Without being too bound by theory, in the catalyst deactivation mechanism referred to as catalyst poisoning, in particular, a specific reaction or accumulation of substances in the reaction feed occurs with or on the active sites of the catalyst for catalysis of the desired main reaction, in this case ODH(E). Subsequently, at least under the conditions required for the desired main reaction, these substances irreversibly bind the catalyst sites active for the main reaction, with the result that they are no longer available for the main reaction.

Thus, catalyst poisoning is characterized in particular by the fact that a deactivation front pushes over the respective catalyst bed in the flow direction, i.e., while initial regions of the catalyst bed (i.e., upstream of the deactivation front in the catalyst bed) are in part already completely or almost completely deactivated, the regions (immediately) downstream of the deactivation front still exhibit their complete or almost complete activity.

During the runtime—in the case of oxidative methods such as ODH(E), typically significantly more than 1 year and up to several years, there is therefore usually a gradual deactivation of the catalyst or reduction in catalyst activity, which is usually compensated for during operation by a gradual increase in the temperature in the reactor by means of correspondingly specified operating parameters. Since the absolute active catalyst mass initially fed into the reactor remains constant, this usually means a loss of selectivity to the products of value at the same reaction rate.

Typical interfering trace components are in particular—as a non-exhaustive list—sulfur compounds, phosphorus compounds, nitrogen compounds, metals and compounds thereof (in particular alkali metals, alkaline earth metals and heavy metals), aluminosilicates, halides (in particular chlorides) and halogen-containing compounds as well as heavy hydrocarbons. In practice, operating agents such as oils, lubricants and greases are also frequently enter the reactor, with corresponding negative consequences. The alkaline earth and heavy metals mentioned may include in particular Na, K, Cs, Mg, Ca, Al, Si, Fe, Cr, Ni, As, Sb, Hg, Pb, and V. The entry of compounds containing oxygen and nitrogen, such as oxygenates, alcohols, carbonyl compounds, amines, nitrogen oxides, etc., as well as heavy hydrocarbons, in particular unsaturated and aromatic compounds are to be considered here, can also have a negative effect.

The origin of the trace components is mostly to be found in the origin or provision of oxygen, ethane and water. On the one hand, these components or their derivatives originate from the corresponding raw material source, i.e., in the case of ODH(E), from the ethane or associated gas source. For alkali and alkaline earth metals (in particular Na, K as well as Mg and Ca) as well as halides (in particular chloride), on the other hand, a steam generation system can also lead to contamination of the steam if a corresponding water treatment is not adequately designed or there are increased concentrations of interfering trace components here due to operational malfunctions.

In particular, however, the steam may also contain metering chemicals which, for example, serve to inhibit corrosion and, in particular, may also contain (highly volatile) nitrogen-containing components. Furthermore, the oxygen source can also contribute to the entry of interfering trace components, e.g., from the ambient air or from process-related contamination.

Therefore, a corresponding feed preparation or treatment is usually carried out upstream of the actual reactor, and can comprise, for example, adsorptive, absorptive and/or distillative steps.

In particular, so-called guard beds, which are usually designed as fixed beds and filled with a suitable guard material, are used to remove trace components. Both adsorptive and reactive mechanisms of action can be used here. Depending on the type and amount of trace components to be removed, the guard beds may be regenerable as well as non-regenerable. Additional apparatus and method steps are therefore required here for feed preparation.

This feed preparation usually concerns the hydrocarbon feed, while for the steam, a corresponding water treatment is carried out upstream of the steam production. In principle, however, the oxygen required for an ODH(E) method according to the invention may also be contaminated with impurities, which makes corresponding additional pre-purification necessary.

Shell-and-tube reactors typically used for ODH(E) with up to several tens of thousands of parallel tubes in large-scale applications are complex and cost-intensive constructions or apparatuses. Thus, for both design and cost reasons, the size and dimensions must be as compact as possible. An important parameter here is the length of the individual reaction tube, which must be utilized as efficiently as possible, which means that its length should be kept as short as possible. In particular, volumes that are only filled with inert material should be kept as small as possible, as they are otherwise of no commercial use.

Thus, as described below, the mass of inert material should be minimized or at least replaced in a useful way. Accordingly, however, in particular "overdimensioning" of the catalyst filling, e.g., in order to be able to compensate for aging and/or poisoning effects, is also to be avoided wherever possible. A reduction in such an inert volume and/or an "overdimensioned" catalyst filling additionally leads to a reduction in pressure drop across the reactor due to the associated reduction in length of the individual reaction tubes, which is significant in particular for "low-pressure" methods such as ODH(E), which is typically performed at less than 10 bar (abs.) or less than 6 bar (abs.).

In principle, it is also conceivable to enlarge the catalyst bed to achieve a longer run time, provided a minimum temperature is observed. In principle, a somewhat lower temperature can be selected at the start of run (SOR) in order to compensate for the deactivation by increasing the temperature. However, due to the effect on the length of the catalyst bed and the associated loss of selectivity already mentioned, this is only partially expedient in practice.

On the other hand, the emptying and filling process for such reactors is also relatively complex. It is thus advantageous to achieve the longest possible run time between two catalyst feeds.

SUMMARY

According to the invention, therefore, one object is to keep the time interval between two catalyst changes as long as possible while at the same time achieving economical production during the run time, i.e., to achieve the highest possible and most constant selectivity or yield of products of value. To this end, it is necessary to minimize adjustments to the reaction conditions, such as, for example the reaction temperature. It is therefore necessary to achieve stabilization of the reaction conditions.

As explained herein, both upstream method steps for feed treatment and an inert preheating zone are conventionally used, which zone, however, is already located within the actual reactor, specifically the respective reaction tube. However, in particular in the case of a shell-and-tube reactor, this means that this inert preheating zone is located in the region of a relatively elaborate structure and that the volume of the reactor is increased by space that is unused in terms of reaction technology. The necessary size of this preheating zone is determined from the specific heat transfer (depending in particular on particle geometry, flow velocity, reactant gas composition and density, viscosity and heat capacity of the reactant gas) and the temperature difference between the feed mixture at the reactor inlet and the required reaction temperature at the beginning of the actual reaction zone.

It is therefore important to keep this region as short as possible and therefore its volume as small as possible and/or to use it beneficially. At the same time, however, the aforementioned upstream measures for feed treatment also mean additional equipment expenditure, which must also be minimized.

According to one embodiment of the invention, a method for producing a target compound includes distributing a feed mixture at a temperature in a first temperature range to a plurality of parallel reaction tubes of a shell-and-tube reactor; subjecting the feed mixture in first tube sections of the reaction tubes to heating to a temperature in a second temperature range; and subjecting the feed mixture in second tube sections of the reaction tubes arranged downstream of the first tube sections to oxidative catalytic conversion using one or more catalysts arranged in the second tube sections. The heating is performed, at least in part, using a catalyst arranged in the first tube sections and having a light-off temperature in the first temperature range.

According to another embodiment of the invention, a plant for producing a target compound has a shell-and-tube reactor which has a plurality of parallel reaction tube having first tube sections and second tube sections arranged downstream of the first tube sections. One or more catalysts are arranged in the second tube sections. The plant has means configured to distribute a feed mixture at a temperature in a first temperature range to the reaction tubes; subject said feed mixture to heating to a temperature in a second temperature range; and subject said feed mixture to an oxidative catalytic conversion in the second tube sections using the one or the more plurality of catalysts arranged in the second tube sections. For at least a part of the heating in the first tube sections, a catalyst is provided which has a light-off temperature in the first temperature range.

WRITTEN DESCRIPTION

Figure 1:
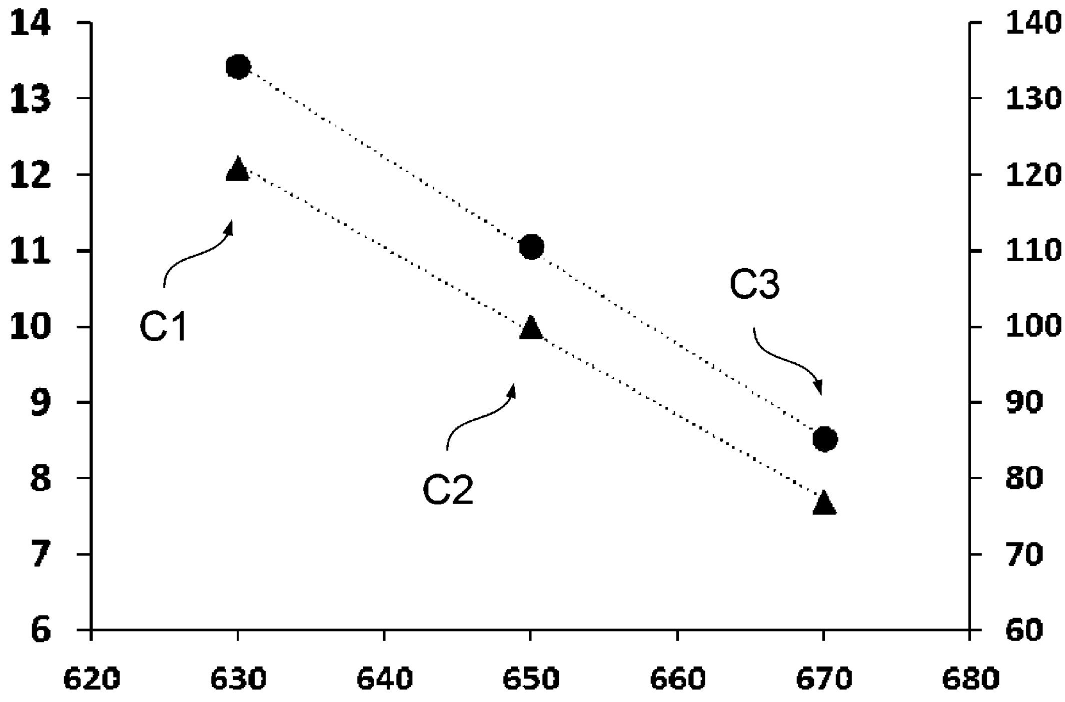
FIG. 1 illustrates different catalyst activities for catalysts obtained at different calcination temperatures.

Typical catalysts for heterogeneous catalysis, in particular for oxidative processes and especially for ODH(E), require a certain minimum temperature, the so-called light-off temperature, for a considerable reaction to take place. According to the prior art, this light-off temperature depends in particular on the catalytically active material used. Since the light-off temperature in conventionally used catalyst beds is above the feed temperature of the feed mixture into the reactor used, the preheating zones of inert material mentioned above are used.

In one embodiment, the invention now utilizes the fact that the activity of a particular catalyst material, and by association the light-off temperature, can be influenced by the production and in particular by a single production step. It was found, in particular for the advantageously used $MoVNb(Te)O_x$ catalysts, that the calcination conditions have a direct influence on their respective activity. Increased activity is accompanied by a reduced light-off temperature. The catalytically active material itself remains in principle the same in terms of composition and can in particular be obtained from the same synthesis approach.

In the aforementioned embodiment, the invention utilizes this by employing a catalyst of advantageously the same type and elemental composition with a corresponding lower light-off temperature and associated higher activity in zones (hereinafter also referred to as “first tube sections”) of the reaction tubes of a shell-and-tube reactor which were previously used for heating to the light-off temperature of the downstream of the corresponding zone and were filled with inert material. As explained below, an inert zone for preheating can therefore be dispensed with in whole or in part, and deactivation of the main catalyst bed(s) arranged downstream (in tube sections referred to herein as “second tube sections”) can be avoided, at least for the most part.

In principle, however, a catalyst which is provided in another way with a higher activity, and thus has a reduced light-off temperature, can also be used within the scope of the invention. Specific examples are mentioned below.

Overall, the invention proposes a method for producing a target compound, in which a feed mixture at a temperature in a first temperature range is distributed to a plurality of parallel reaction tubes of a shell-and-tube reactor, is subjected in first tube sections of the reaction tubes to heating to a temperature in a second temperature range, and is subjected in second tube sections of the reaction tubes arranged downstream of the first tube sections to oxidative catalytic conversion using one or more catalysts arranged in the second tube sections. According to the invention, the heating is performed, at least in part, using a catalyst arranged in the first tube sections and having a light-off temperature in the first temperature range. In other words, the invention thus proposes to at least partially dispense with a preheating zone with inert material and instead provide an upstream catalyst bed with a lower light-off temperature or higher activity. It should already be pointed out at this juncture that an inert material need not be completely dispensed with in the scope of the invention. This can be used, for example, for uniform distribution of the respective gas flows over the entire cross-section of the reaction tubes at a suitable point.

In the scope of the invention, the first temperature range can be in particular 170 to 280° C., preferably 200 to 270° C. and particularly preferably 220 to 260° C., the second temperature range preferably 280 to 450° C. and particularly preferably 300 to 400° C. Irrespective of specific values, the temperature in the first temperature range (and thus the light-off temperature) is in particular 30 to 110 K, preferably 40 to 80 K and particularly preferably 40 to 60 K below the temperature in the second temperature range (of the main bed). In practice, there is a profile in the respective temperature ranges, i.e., heating up to a respective hotspot, and then falling again. The “light-off temperature” is understood in particular to mean the temperature at which the catalyst, under technically relevant conditions, converts more than 10% of the reactant under consideration, i.e., an alkane in the case of ODH, and ethane in the case of ODH(E).

The disadvantages mentioned at the outset can be overcome by using the invention. In particular, by using the invention, volumes that are otherwise only filled with inert material and thus have no commercial benefit whatsoever can be kept small compared to the prior art, or possibly avoided completely. The reduction in the inert volume leads to a reduction in the pressure drop across the reactor due to the associated reduction in the length of the individual reaction tubes, which is particularly advantageous in particular for methods such as ODH(E). For further advantages, reference is made to the explanation of the objects of the invention, which are at least partially achieved by the proposed measures.

The catalyst arranged in the first tube sections and the one or at least one of the multiple catalysts arranged in the second tube sections advantageously contain at least the metals molybdenum, vanadium, niobium and optionally tellurium, in particular in the form of a corresponding mixed oxide, since, as has been demonstrated in accordance with the invention, the aforementioned advantageous effects are particularly pronounced with corresponding catalysts.

The catalyst arranged in the first tube sections and the one or at least one of the multiple catalysts arranged in the second tube sections can furthermore be produced according to the invention at least partially from the oxides of the corresponding metals. The catalyst production is therefore extremely cost-effective due to the readily available starting materials.

The catalyst arranged in the first tube sections and the one or at least one of the multiple catalysts arranged in the second tube sections advantageously have an identical elemental composition, as already discussed. This enables simple production of the corresponding catalysts, the differences between which are merely due to the different manufacturing process. According to the understanding applied here, an “identical elemental composition” should still be present even if the contents of the individual elements or their compounds do not differ by more than 10%, 5% or 1% between the different catalysts.

Advantageously, the catalyst arranged in the first tube sections has an activity which is more than 10% higher than the one or at least one of the multiple catalysts arranged in the second tube sections due to different calcination intensities. The activity can also be, for example, 20%, 30% or 40% higher. Conversely, the catalyst arranged in the first tube sections advantageously has, due to the different calcination intensities, a light-off temperature that is more than 3 K lower, preferably more than 5 K lower, further preferably more than 10 K lower, and particularly preferably more than 15 K lower. A calcination intensity is in particular conditioned by the calcination procedure, but also for example a particularly intensive, e.g., long-lasting, calcination.

Thus, according to the invention, the previously usual preheating zone in the reactor with inert material can be completely or partially filled with a catalyst having the same catalytically active material. In this case, however, a material is advantageously selected that has a very low light-off temperature which ideally corresponds to the temperature of the reactant mixture at the reactor inlet. In accordance with the invention, if desired, a short inert layer can be provided at the reactor tube inlet, i.e., upstream of the aforementioned very active catalyst layer having the low light-off temperature (and thus upstream of the first tube sections), in order to achieve formation of a defined flow profile in the reactor tube and thus defined starting conditions (so-called inlet path). The length of such an inlet path is usually at least 10 times the equivalent diameter of an inert particle used, but at most typically less than 50 cm, in particular less than 30 cm or less than 20 cm.

A possible inert inlet path is followed by a reactive preheating path (in the form of the first tube sections). An essential function of this reactive preheating path provided according to the invention is that any catalyst poisons which may be contained in the reactant flow can already react here with the catalytically active material and/or are adsorbed, since the catalytically active material in the preheating zone advantageously corresponds to that in the following main reaction zone(s) (in the second tube sections). Preferably, these one or more following main reaction zones are designed with multiple catalyst beds with a volumetric activity of the beds increasing from the reaction tube start to the reaction tube end, i.e., in the direction of flow (e.g., through different dilution of the catalyst particles having the same basic activity with suitable inert material; cf. in this respect WO 2019/243480 A1, as already discussed).

For the reactive preheating path (i.e., in the first tube sections), in particular an active catalyst material is used according to the invention, which in its chemical composition corresponds to the material in the following main reaction zone(s) (i.e., the second tube sections), but is even more active, as already explained in other words. Such an even more active $MoVTeNbO_x$ catalyst is described, for example, in WO 2018/141652 A1 or WO 2018/141653 A1. In a preferred embodiment, the volumetric activity of the reactive preheating bed has at least a similar value to the most active main reaction zone. However, in a particularly preferred embodiment, the active material of the reactive preheating zone is subjected during production thereof to a lower calcination intensity, for example calcined at a lower temperature, and thus has a higher basic activity than the catalyst material of the main reaction zones. Alternatively, however, the activity can also be increased by adjusting the composition of the catalyst, as described for example in WO 2018/141652 A1. In particular, the volumetric activity of the reactive preheating zone may in this case exceed the value of the highest volumetric activity of the one or more main reaction zones.

In this case, the higher volumetric activity is usually accompanied by a higher pore volume and/or a higher BET surface area and, in particular, a lack of inert dilution. The BET surface area is the mass-specific surface area, which is calculated from experimental data according to known methods and usually expressed in the unit square meter per gram ($m^2 \cdot g^1$). BET measurement is known to the person skilled in the art from relevant textbooks and standards, for example DIN ISO 9277:2003-05, “Determination of the specific surface area of solids by gas adsorption using the BET method (ISO 9277:1995)”. However, this is not a necessary requirement for the implementation of the invention, but relates to a possible embodiment. The specific pore volume of a catalyst can be determined, for example, by means of nitrogen physisorption measurements.

In a corresponding embodiment, a pore volume and/or a BET surface area in the first tube sections is above, in particular 15 to 60% above, a maximum pore volume and/or a maximum BET surface area in the second tube sections.

The length of such a reactive preheating path (i.e., of the first tube sections) is preferably at least ten times the equivalent diameter of a catalyst particle used, but preferably less than 40 cm or less than 30 cm, particularly preferably between 5 and 25 cm. In addition, an embodiment in which the length of the reactive preheating in relation to the main reaction zone(s) is less than 0.1 in total, preferably less than 0.07, and particularly preferably less than 0.04, is in particular relevant for the technical design.

In other words, a length of a region in which the catalyst is arranged in the first tube sections is less than 40 cm in absolute dimensions and/or this length is less than 0.1 relative to a total length of a region in which the one or the multiple catalysts is or are arranged in the second tube sections.

A higher basic activity of the otherwise identical chemical material implies that the number of active sites of such a material is larger. A larger number of active sites in the reactive preheating path (i.e., the first tube sections) increases the uptake capacity for substances that can deactivate the catalyst. As a result, the service life of the main reaction zones (in the second tube sections) is extended with the same reactant mole flow. This is particularly important since the function of this reactive preheating zone consists in protecting the subsequent (downstream) main reaction zones from substances that deactivate the catalyst in the main reaction zones, in particular by poisoning.

As has already been stated, in the catalyst deactivation mechanism of so-called catalyst poisoning, a specific reaction or accumulation of substances in the feed occurs at the sites of the catalyst which are active for the actual catalysis of the desired main reaction, in this case in particular oxidative dehydrogenation, in particular of ethane, ODH(E), in the course of which these substances bind irreversibly to the catalyst sites active for the main reaction, at least under the conditions necessary for the desired main reaction, meaning that said sites are no longer available for the actual main reaction. So that the bed upstream of the main reaction zones can fulfill its function, it is particularly advantageous if this catalyst material lights off at a lower temperature, i.e., catalyzes precisely these reactions. Otherwise, no specific reaction with the possible catalyst poisons will occur either.

Surprisingly and according to the invention, however, the reactive preheating path, although a much more active catalyst is used, has no appreciable influence on the overall reactor performance, i.e., the performance of the totality of the reactive beds (reactive preheating zone and one or more main reaction zones), in terms of conversion and selectivity to commercial products, as can be seen from FIG. 2, which is explained below. This figure and the accompanying Table 3 are referred to here. The function of the reactive preheating zone is thus to be viewed in particular as that of advantageously extending the service life of the main reaction zones. As explained there, within the scope of the invention, the coolant temperature can optionally be raised as deactivation increases.

The functionality of the reactive preheating zone can be monitored by means of devices which record values that are a measure of the catalyst activity. Particularly suitable for this purpose is monitoring of the bed temperature of this reactive preheating zone at at least one point in the bed of this reactive preheating zone, but preferably distributed over multiple points in the bed of the preheating zone. Similarly, the activity of the main reaction zone can also be detected very easily online (in addition, of course, to online monitoring of the oxygen content at the reactor outlet and complete regular analyses of the process gas composition, although these are not usually performed online).

In particular, in summary again, the embodiment of the catalysts according to the invention may be such, due to being manufactured differently, that a volumetric activity in the first tube sections is above a maximum volumetric activity in the second tube sections.

As mentioned, the invention can be used in particular in connection with an ODH of alkanes such that the feed mixture advantageously contains oxygen and an alkane, in particular having two to six carbon atoms, and the oxidative conversion is performed as an oxidative dehydrogenation of the alkane. In an ODH employed with particular advantages, ethane is used as the alkane and an oxidative dehydrogenation of ethane (ODHE) is performed.

The oxidative conversion is advantageously carried out at a temperature of the catalyst in a range between 24° and 500° C., preferably between 28° and 450° C., in particular between 30° and 400° C.

The feed mixture is advantageously fed to the reactor at a pressure in a pressure range from 1 to 10 bar (abs.), in particular from 2 to 6 bar (abs.). This is therefore a method operating at comparatively low pressure, in which the advantages of the shortened reaction tube lengths already mentioned above are obtained in a particular way.

With particular advantage, within the scope of the invention, a water content can be set in the feed mixture which can be between 5 and 95 vol %, particularly between 10 and 50 vol % and further particularly between 14 and 35 vol %. As also disclosed, for example, in EP 3 558 910 B1 of the applicant, it is also possible, for example, to determine at least one characteristic variable indicating an activity of the or one of the catalysts and, on this basis, to set an amount of water in the reaction feed flow on the basis of the at least one determined characteristic variable.

In particular, an embodiment in which the feed mixture contains ethane and in which the molar ratio of water to ethane in the feed mixture is at least 0.23 may be advantageous.

The invention can be applied regardless of how the cooling medium is guided (i.e., in co-current or counter-current). When the cooling medium, in particular a molten salt, is guided in counter-current, a particular additional advantage can be achieved, since in this case the heat of reaction from the main reaction can be partially utilized in the reactive preheating zone. Likewise, different cooling circuits in combination with different catalyst layers are conceivable (as also indicated in more detail still in WO 2019/243480 A1).

There is a particular advantage if the reactor is designed in such a way that the reactor in the region of the reactive preheating, i.e., the first tube sections, is explicitly additionally cooled in a different way, i.e., in said region there is the option of a separate cooling circuit (possibly even with a different coolant flow direction). The advantage of this is targeted temperature adjustment and thus activity adjustment in the reactive preheating zone. As a result, this zone can, for example, also be explicitly "switched on" by corresponding heat input, or "switched off" if not required or only required to a small extent.

In other words, in one embodiment, the invention proposes that the reaction tubes are cooled using one or more cooling media flowing around the reaction tubes. In this case, the first tube sections and the second tube sections can be cooled in a particularly advantageous manner using different cooling media, the same cooling medium in different cooling media circuits, and/or the same or different cooling media in different or the same flow directions.

The invention also relates to a plant for producing a target compound, having a shell-and-tube reactor which has a plurality of parallel reaction tubes having first tube sections and second tube sections arranged downstream of the first tube sections, wherein one or more catalysts are arranged in the second tube sections, and the plant has means configured to distribute a feed mixture at a temperature in a first temperature range to the reaction tubes, to subject said feed mixture to heating to a temperature in a second temperature range, and to subject said feed mixture to an oxidative catalytic conversion in the second tube sections using the one or the multiple catalysts arranged in the second tube sections.

According to the invention, for at least a part of the heating in the first tube sections, a catalyst is provided which has a light-off temperature in the first temperature range.

For further features and advantages of the plant proposed according to the invention, reference is expressly made to the above explanations. In corresponding embodiments, the plant is in this respect configured in particular to perform a method as has already been explained above, likewise in various embodiments. The explanations apply accordingly.

The invention is further explained below with reference to examples corresponding to embodiments of the invention and comparative examples not in accordance with the invention, as well as associated figures and tables.

In embodiments, as mentioned, the invention utilizes the fact that the activity of a particular catalyst material, and by association the light-off temperature, can be influenced by the production. The catalytically active material itself remains in principle the same in terms of composition and can in particular be obtained from the same synthesis approach. This surprising effect was found in a catalytic test of $MoVNb(Te)O_x$ catalyst material with the same synthesis approach and thus the same stoichiometry (element composition), but different calcination temperatures.

In this context, the catalyst material can in principle be produced as described in DE 10 2017 000 861 A1 in Example 2. Here, the suitable metal oxides in each case can be subjected to hydrothermal synthesis.

In the method used in DE 10 2017 000 861 A1, which can also be used in the scope of the invention, $TeO_2$ was slurried in 200 g of distilled water and ground in a planetary ball mill with 1 cm diameter balls ($ZrO_2$). The portion was then transferred to a beaker with 500 mL of distilled water. $Nb_2O_5$ was slurried in 200 g of distilled water and ground in the same ball mill. The portion was then transferred to a beaker with 500 mL of distilled water. The next morning, the temperature was raised to 80° C., and 107.8 g of oxalic acid dihydrate was added to the $Nb_2O_5$ suspension, which was stirred for about 1 h. 6 L of distilled water was placed in an autoclave (40 L) and heated to 80° C. with stirring (stirrer speed 90 rpm). When the water reached the temperature, 61.58 g of citric acid, 19.9 g of ethylene glycol, 615.5 g of $MoO_3$, 124.5 g of $V_2O_5$, the ground $TeO_2$ and the ground $Nb_2O_5$ in oxalic acid were added successively. 850 mL of distilled water was used to transfer and rinse the vessels. The total amount of water in the autoclave was 8.25 L. Nitrogen was then added on top. Hydrothermal synthesis was performed in a 40 L autoclave at 190° C./48 h. After synthesis, filtering was performed using a vacuum pump with blue sand filter and the filter cake was washed with 5 L of distilled water.

Drying was carried out at 80° C. in a drying oven for 3 days and then the product was ground in an impact mill. A solid yield of 0.8 kg was obtained. Subsequent calcination was carried out at 280° C. for 4 h in air (heating rate 5° C./min air: 1 L/min). Activation was carried out in a retort at 600° C. for 2 h (heating rate 5° C./min nitrogen: 0.5 L/min).

However, unlike the method described above, the graduated calcination temperatures listed in Table 1 were used. Furthermore, the catalysts listed in Table 1 were activated in a rotary kiln rather than in the retort. The catalysts obtained are denoted as 1 to 3. The specific surface area according to BET as given in Table 1 and the pore volume refer to the calcined catalyst material before tabletting.

TABLE 1

| Catalyst sample | Cat. 1 | Cat. 2 | Cat. 3 |
|---|---|---|---|
| Calcination temperature of the catalyst [° C.] | 630 | 650 | 670 |
| Specific surface area (according to BET) [$m^2/g$] | 11 | 9.8 | 7.1 |
| Specific pore volume [$cm^3/g$] | 0.0533 | 0.0405 | 0.0293 |
| Reaction temperature window [° C.] | 230-295 | 270-300.5 | 295-310 |
| Ethane conversion range, measured for the reaction temperature window [%] | 4.4-47.5 | 17.9-46.2 | 30.0-43.9 |
| Number of different temperature levels | 8 | 4 | 4 |
| Light-off temperature [° C.] (calculated) = temperature for 10% ethane conversion | 251.0 | 255.7 | 260.0 |

The catalysts produced in this way were tested with respect to their activity in a test plant 1 under exactly identical conditions (filled catalyst amount of 46 g, system pressure of 3.5 bar (abs.), composition of the reaction feed of ethane to oxygen to water (vapor) of 55.3 to 20.7 to 24 (in each case mol %), GHSV of 1140 ($NL_{gas}$/h)/$L_{catalyst}$). The corresponding experimental reactor (usable length 0.9 m, inner diameter of reaction chamber 10 mm) is designed as a double tube. The heating or cooling is carried out with the aid of a thermal oil bath, wherein the thermal oil is pumped through the outer chamber of the reactor and thus heats or also simultaneously cools the inner chamber/reaction zone (the conversion is an exothermic reaction). At an oil bath temperature of 295° C., clear absolute and relative activity gradations of +21% and −23% (relative in each case) were found for the differently calcined catalysts compared with the base case (standard calcination temperature of 650° C.).

The activity gradations are illustrated in FIG. 1, in which the activity in the form of ethane conversion in moles per liter of catalyst and hour (i.e., the activity per catalyst volume) is depicted on the left vertical axis (circles in the diagram) and the relative activity in percent is depicted on the right vertical axis (triangles in the diagram) in relation to the calcination temperature on the horizontal axis. The values obtained for the respective catalysts or catalyst samples according to Table 1 are shown as C1, C2 and C3.

Proceeding from FIG. 1, it is to be expected that the light-off temperatures of these differently calcined catalysts also differ, i.e., that the most active material also has the lowest light-off temperature. This is confirmed by Table 1. The light-off temperature is defined here as the temperature at which the ethane conversion is 10%.

For the catalyst sample, catalyst 1, this light-off temperature can be read almost directly from the experimental data (at 250° C. reaction temperature—this corresponds to the temperature at the start of the catalyst bed and the temperature of the thermal oil bath—the ethane conversion was 9.6%), but not for the other two samples, catalyst 2 and 3, since the conversion range investigated there was smaller. However, for all catalyst samples listed in Table 1, the conversions were determined at at least 4 different temperatures (cf. number of different temperature levels in Table 1), and the number of conversions and temperature levels were sufficiently far apart for all catalyst samples.

Thus, it was possible to create an Arrhenius plot for each of the catalyst samples, i.e., a plot of the natural logarithm of the reaction rate constant against the reciprocal of the reaction temperature (in Kelvin). The creation of an Arrhenius plot is in principle known to the person skilled in the art.

The Arrhenius plot provides a straight line with different parameters (slope and intercept) for each of the catalyst samples. With the aid of the respective straight-line equation, it is possible to determine the associated reaction rate constant for a specified ethane conversion and, from this, the corresponding reaction temperature. The corresponding reaction temperature determined for an ethane conversion of 10% is given in the line "Light-off temperature [° C.] (calculated)=temperature for 10% ethane conversion" in Table 1.

On the basis of the observed trend in the activities and the light-off temperatures of catalysts 1 to 3 as a function of the calcination temperature (cf. FIG. 1 and Table 1), it can be assumed that the activity of the catalysts with lower calcination temperatures can be further increased, at least within certain limits, as long as the calcination temperature and duration, i.e., the calcination intensity, are sufficient for a solid/crystal phase to form which is sufficiently stable for catalysis.

Indeed, a further, significant increase in activity and thus a further, significant shift in light-off temperature to lower values was observed for a catalyst that had been calcined at 400° C. (catalyst 4). This catalyst was tested in a test plant 2 with the following test parameters: the test plant 2 consists of a tubular reactor with a usable length of 1 m and an internal diameter of 25 mm. The reactor is heated and simultaneously cooled by means of a salt bath fluidized with nitrogen in which the reactor is immersed. For technical reasons, air was used as oxidant instead of pure oxygen; furthermore, this test plant 2 could only be operated under atmospheric pressure. The other test conditions in this setup were as follows: infilled catalyst amount of 337 g, reaction feed composition of ethane to nitrogen to oxygen to water (vapor) of 11.1 to 46.7 to 6.8 to 35.4 (mol % each), GHSV of 418 $(NL_{gas}/h)/L_{catalyst}$. For comparison, catalyst 2 (see FIG. 1 and Table 2) was also tested in this test plant 2 under the same conditions. The test results are listed in Table 2.

A significantly higher activity of catalyst 4 compared to catalyst 2 is proven from the direct experimental comparison in test plant 2 (cf. Table 2): catalyst 2 has an ethane conversion of approximately 67% at a salt bath temperature of 322° C. Catalyst 4, on the other hand, only requires a salt bath temperature of 302° C. for a conversion of 64% and still has a significantly higher conversion at this temperature than catalyst 2 at a higher temperature of 310° C. (ethane conversion for catalyst 2 of 53%).

To estimate the light-off temperature of catalyst 4 under the technically much more relevant conditions of test plant 1, the following procedure was followed: using the ethane conversion determined at the salt bath temperature given in Table 2 and the other test conditions given, a reaction rate constant corresponding to this temperature was calculated. The procedure for this is in principle known to the person skilled in the art.

This reaction rate constant served as the starting point for determining a corresponding Arrhenius straight line. Since only one measuring point was available for catalyst 4, the same slope of the Arrhenius straight line was used as determined for the test conditions from test plant 1, assuming that the apparent activation energy is independent of the test conditions.

Using this Arrhenius straight line determined for catalyst 4, and taking into account the inaccuracy resulting from this procedure, a resulting range for the light-off temperature of catalyst 4 of approx. 233-242° C. was estimated for the technically relevant test conditions of test plant 1. Despite the relatively high uncertainty with regard to the light-off temperature for catalyst 4 under the technically relevant conditions, it can be seen that the range of the light-off temperature for catalyst 4 is significantly lower than the light-off temperature of catalyst 1; accordingly, catalyst 4 also has the highest activity.

TABLE 2

| Catalyst sample | Catalyst 2 | | Catalyst 4 |
|---|---|---|---|
| Calcination temperature of the catalyst [° C.] | 650 | | 400 |
| Specific surface area (according to BET) [m²/g]* | 9.8 | | 27 |
| Specific pore volume [cm³/g]* | 0.0405 | | 0.11 |
| Salt bath temperature [° C.] | 310 | 322 | 302 |
| Ethane conversion | 53.0 | 67.1 | 64.2 |

The values in Table 2 marked with an asterisk refer to the pure MoVNbTe oxide catalyst powder (before tabletting). For tabletting, silica and wax are added as tabletting excipients. The porosity of the silica co-determines the porosity of the final catalyst shaped bodies, which means that the exact value of said porosity differs. However, the nitrogen pore volume of the actual catalyst powder before tabletting is correlated with the activity.

The findings according to the invention explained above are surprising. The different activity and light-off behavior of the catalyst samples according to the invention can surprisingly be correlated with the data from the catalyst characterization (cf. Table 1 and 2). By lowering the calcination temperature during catalyst production, an increase in the specific surface area, and, even more significantly, the specific pore volume can be achieved as a novel finding. However, while higher activity is usually accompanied by reduced selectivity, surprisingly, in the scope of the invention, high or even constantly high selectivity of the overall reaction bed can still be achieved.

Figure 2:
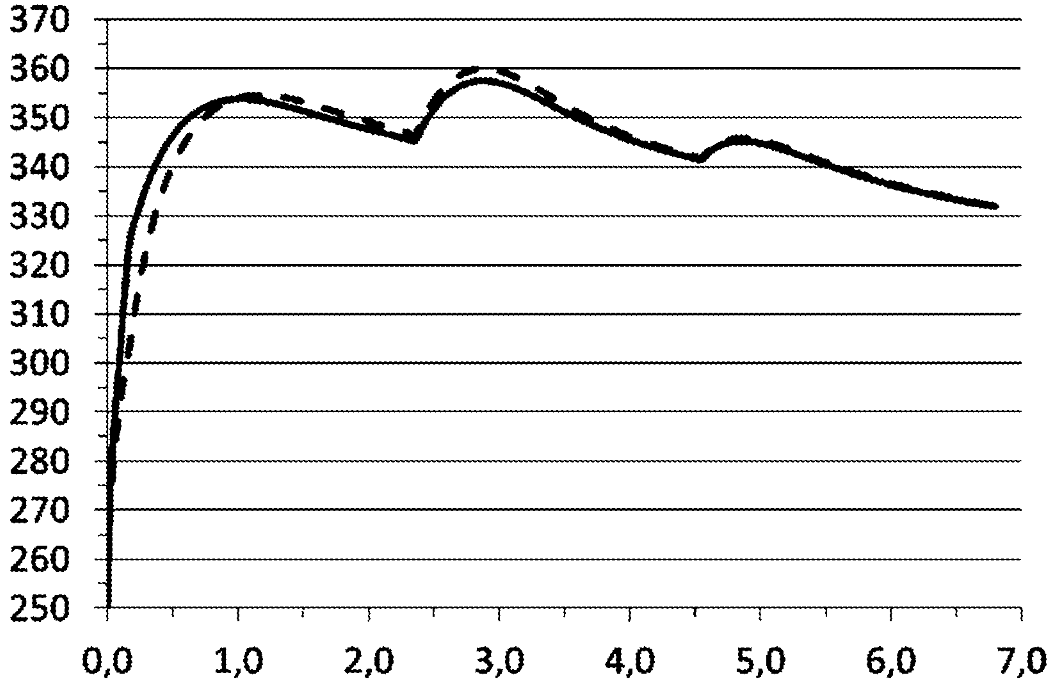
FIG. 2 illustrates temperature profiles for a three-stage catalyst bed with a reactive preheating zone according to one embodiment of the invention.

FIG. 2 illustrates temperature profiles for a three-stage catalyst bed of the main reaction zone based on a catalyst 2 (see above) with a reactive preheating zone, wherein the material of the reactive preheating zone according to the particularly preferred embodiment has approximately 1.2 times the basic activity of the catalyst material of the main reaction zone. In each case, temperature profiles obtained at the SOR (beginning of the investigation period with fresh catalysts, "start of run", solid line) and EOR (end of the investigation period, "end of run", dashed line) are illustrated in ° C. on the vertical axis in relation to a reaction tube length in m on the horizontal axis.

For the design, care was taken to ensure that both the composition and the total mass flow rate of the reaction mixture at the reactor tube inlet, and thus the loading of the main reaction zones (i.e., the WHSV of the main reaction zone), were identical. In the first case (SOR), the reactive preheating zone exhibits its full activity, whereas in the second case (EOR), the reactive preheating zone is completely deactivated, i.e., inert, e.g., due to poisoning, whereas, in contrast, the catalyst beds of the main reaction zone continue to exhibit their full activity (i.e., the activity that occurs after a typical run-in period), which applies to the catalyst deactivation mechanism "poisoning" as explained above. The same coolant temperature was used for both cases. The coolant was guided in counter-current to the reaction gas. It can be seen that during the course of deactivation of the reactive preheating path, an unchanged reactor function can be maintained without the need to adjust operating parameters, e.g., the coolant temperature. Usually, the coolant temperature must be raised as deactivation progresses. In the scope of the invention, this can additionally be carried out optionally, but in this case much later and/or to a lesser extent, e.g., after extensive deactivation of the reactive preheating zone, which prolongs the overall service life of a corresponding technical reactor.

In the following table, the parameters illustrated in FIG. 2 and further parameters are again summarized in tabular form.

TABLE 3

| | Cat. 2-SOR | Cat. 2-EOR |
|---|---|---|
| Conversion of ethane | 49.6 | 49.8 |
| Selectivity to ethylene | 82.0 | 82.3 |
| Selectivity to acetic acid | 12.9 | 12.6 |
| Selectivity to carbon monoxide | 3.6 | 3.6 |
| Selectivity to carbon dioxide | 1.5 | 1.5 |

Figure 3:
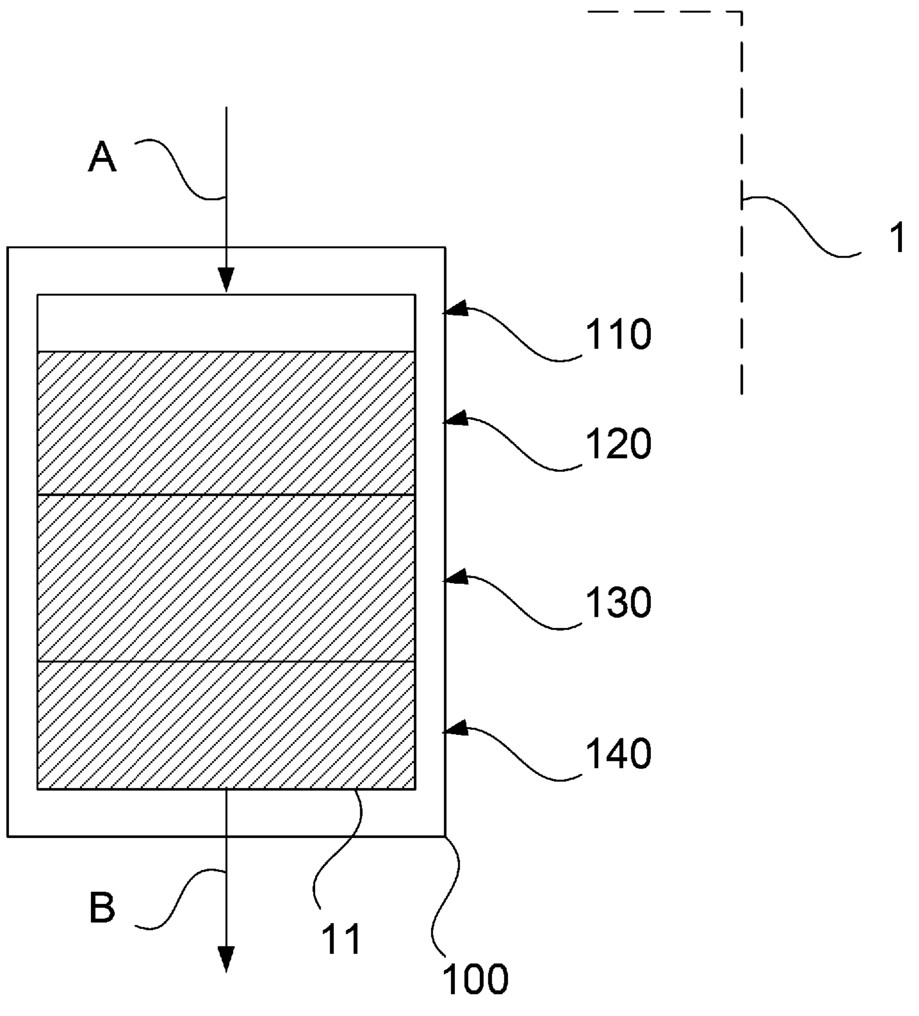
FIG. 3 illustrates a plant according to an embodiment of the invention in a simplified schematic depiction.

FIG. 3 illustrates a plant for producing olefins in accordance with an embodiment of the invention in the form of a highly simplified plant diagram that is designated overall by 1. Plant 1 is only indicated schematically in this case. In particular, the basic arrangement of the preheating zone and the subsequent reaction zone(s) is illustrated using a greatly enlarged reaction tube 11, not drawn to scale, in a shell-and-tube reactor 100. Although a plant 1 for ODHE is described below, as mentioned, the invention is also suitable for use in ODH of higher hydrocarbons. In this case, the following explanations apply accordingly.

As mentioned, plant 1 has a shell-and-tube reactor 100 to which, in the example shown, a feed mixture A containing ethane and obtained in any manner is fed. The feed mixture A may contain, for example, hydrocarbons withdrawn from a rectification unit not shown. The feed mixture A can also be preheated, for example, and treated in another way. The feed mixture A may already contain oxygen and, optionally, a reaction moderator such as water vapor, but corresponding media may also be added upstream or in the shell-and-tube reactor 100, as is not separately illustrated. A product mixture B is withdrawn from the tubular reactor 100.

Figure 4:
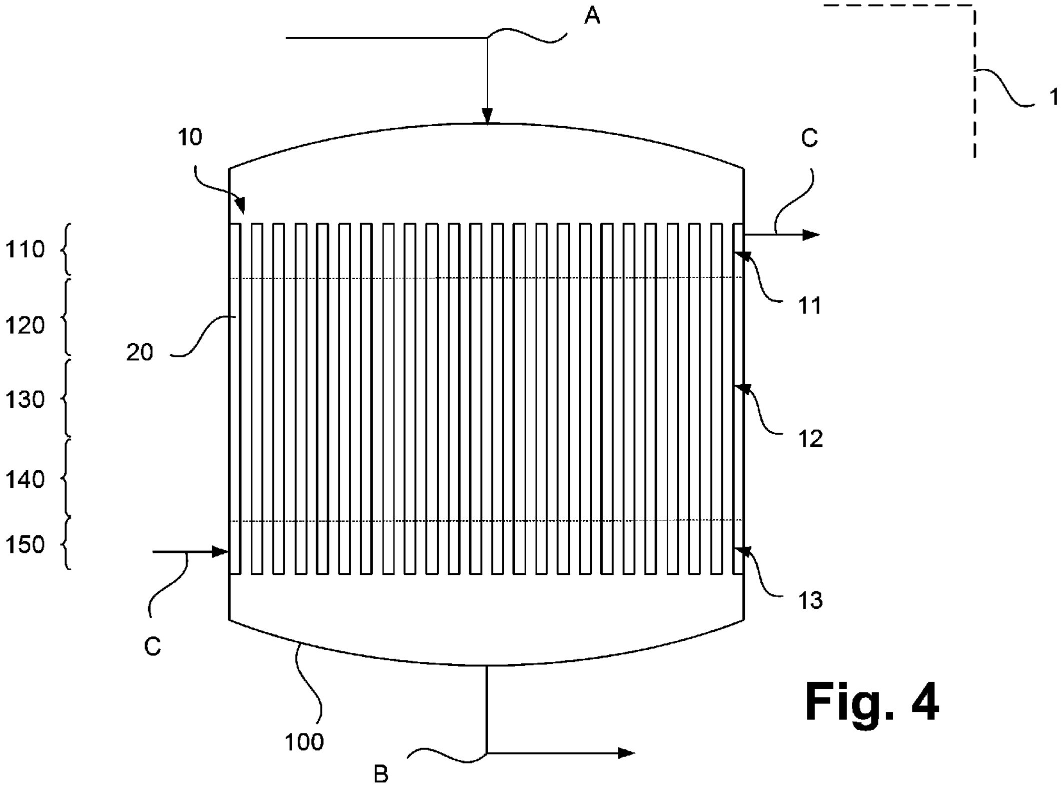
FIG. 4 illustrates a reactor according to an embodiment of the invention in a simplified schematic depiction.

The shell-and-tube reactor 100, shown in detail in FIG. 4, has a plurality of parallel reaction tubes 10 (only partially designated) which extend through a preheating zone 110 and then through a plurality of reaction zones 120, 130, 140, three in the example shown. The reaction tubes 10 are surrounded by a jacket region 20 through which, in the example, a coolant C of the type explained is guided. The illustration is greatly simplified because, as mentioned, the reaction tubes 10 may be cooled using a plurality of cooling media, if necessary, flowing around the reaction tubes 10, or different tube sections may be cooled using different cooling media, the same cooling media in different cooling media circuits, and/or the same or different cooling media in the same or different flow directions.

After being fed into the shell-and-tube reactor, the feed mixture A is suitably distributed to the reaction tubes 10 at a temperature in a first temperature range. The reaction tubes each have first tube sections 11 located in the preheating zone 110 and second tube sections 12 located in the reaction zones 120, 130 and 140.

Heating to a temperature in a second temperature range is carried out in the first tube sections 11 of the reaction tubes 10, and in the second tube sections 12 ofthe reaction tubes 10 arranged downstream of the first tube sections 11, the correspondingly preheated feed mixture A is subjected to oxidative catalytic conversion using one or more catalysts arranged in the second tube sections 12.

The heating is performed at least in part using a catalyst arranged in the first tube sections 11 which has a light-off temperature in the first temperature range and the use of which already leads to a partial conversion. For further details, in particular concerning provision of additional inert zones, reference is expressly made to the above explanations.

Subsequent method steps or plant components are not illustrated. In particular, the process gas can be brought into contact with wash water or a suitable aqueous solution, as a result of which the process gas can be cooled and acetic acid can be washed out of the process gas. The process gas, which is at least largely freed of water and acetic acid, may be further treated and undergo separation of ethylene. Ethane contained in the process gas can be recycled into the reactor 100.

The invention claimed is:

1. A method for producing a target compound, comprising:

distributing a feed mixture at a temperature in a first temperature range to a plurality of parallel reaction tubes of a shell-and-tube reactor;

subjecting the feed mixture in first tube sections of the reaction tubes to heating to a temperature in a second temperature range; and subjecting the feed mixture in second tube sections of the reaction tubes arranged downstream of the first tube sections to oxidative catalytic conversion using one or more catalysts arranged in the second tube sections;

wherein the heating is performed, at least in part, by exothermically reacting the feed mixture with a catalyst arranged in the first tube sections and having a light-off temperature in the first temperature range, wherein the feed mixture contains oxygen and an alkane and wherein the oxidative conversion is performed as oxidative dehydrogenation of the alkane.

2. The method according to claim 1, in which a volumetric activity in the first tube sections is above a maximum volumetric activity in the second tube sections.

3. The method according to claim 2, in which a pore volume and/or a BET surface area in the first tube sections is above a maximum pore volume and/or above a maximum BET surface area in the second tube sections.

4. The method according to claim 1, in which the catalyst arranged in the first tube sections has an activity that is more than 10% higher than the one or at least one of the multiple catalysts arranged in the second tube sections due to different calcination intensities.

5. The method according to claim 1, in which a length of a region in which the catalyst is arranged in the first tube sections is less than 0.1 relative to a total length of a region in which the one or the multiple catalysts are arranged in the second tube sections.

6. The method according to claim 1, in which the catalyst arranged in the first tube sections and the one or at least one of the multiple catalysts arranged in the second tube sections contain at least the metals molybdenum, vanadium, and niobium.

7. The method according to claim 6, in which the catalyst arranged in the first tube sections and the one or at least one of the multiple catalysts arranged in the second tube sections are at least partially produced from the oxides of the metals.

8. The method according to claim 7, in which the catalyst arranged in the first tube sections and the one or at least one of the multiple catalysts arranged in the second tube sections have an identical elemental composition.

9. The method according to claim 6, in which the catalyst arranged in the first tube sections and the one or at least one of the multiple catalysts arranged in the second tube sections further contain tellurium.

10. The method according to claim 6, in which the catalyst arranged in the first tube sections and the one or at least one of the multiple catalysts arranged in the second tube sections are at least partially produced from the oxides of the metals.

11. The method according to claim 10, in which the catalyst arranged in the first tube sections and the one or at least one of the multiple catalysts arranged in the second tube sections have an identical elemental composition.

12. The method according to claim 6, in which the catalyst arranged in the first tube sections and the one or at least one of the multiple catalysts arranged in the second tube sections have an identical elemental composition.

13. The method according to claim 1, in which the first temperature range is 170 to 280° C., and/or in which the second temperature range is 280 to 450° C.

14. The method according to claim 1, in which the temperature in the first temperature range is 30 to 110 K below the temperature in the second temperature range, and/or in which the feed mixture is fed to the reactor at a pressure in a pressure range of 1 to 10 bar (abs.).

15. The method according to claim 1, in which the feed mixture contains a water content between 5 and 95 vol %, wherein the molar ratio of water to ethane in the feed mixture is at least 0.23.

16. The method according to claim 1, in which the reaction tubes are cooled using one or more cooling media flowing around the reaction tubes.

17. The method according to claim 16, in which the first tube sections and the second tube sections are cooled using different cooling media, the same cooling medium in different cooling media circuits, and/or the same or different cooling media in different or the same flow directions.

18. The method according to claim 1, in which the alkane is ethane, and in which the oxidative dehydrogenation of the alkane is oxidative dehydrogenation of ethane.

19. A plant for producing a target compound, having:

a shell-and-tube reactor which has a plurality of parallel reaction tubes having first tube sections and second tube sections arranged downstream of the first tube sections, wherein one or more catalysts are arranged in the second tube sections;

a feed source configured to provide a feed mixture comprising an alkane and oxygen to the shell-and-tube reactor; and means configured to:

distribute the feed mixture at a temperature in a first temperature range to the reaction tubes;

subject said feed mixture to heating to a temperature in a second temperature range; and subject said feed mixture to an oxidative dehydrogenation of the alkane in the second tube sections using the one or the more plurality of catalysts arranged in the second tube sections;

wherein for at least a part of the heating in the first tube sections, a catalyst is provided which has a light-off temperature in the first temperature range and which is configured to exothermically react with the feed mixture.

* * * * *